United States Patent [19]

Mente

[11] Patent Number: 4,997,471
[45] Date of Patent: Mar. 5, 1991

[54] THICKENING AQUEOUS SYSTEMS
[75] Inventor: Donald C. Mente, Grosse Ile, Mich.
[73] Assignee: BASF Corporation, Parsippany, N.J.
[21] Appl. No.: 179,532
[22] Filed: Apr. 8, 1988

Related U.S. Application Data

[63] Continuation-in-part of Ser. No. 840,432, Mar. 17, 1986, abandoned.
[51] Int. Cl.$^5$ .................... A01N 25/02; A01N 43/48; A01N 47/30; A01N 29/00
[52] U.S. Cl. ............................................ 71/65; 71/93; 71/120; 71/118; 71/126
[58] Field of Search .................. 71/DIG. 1, 93, 112, 71/3, 120, 118, 126, 125; 568/625, 624

[56] References Cited

U.S. PATENT DOCUMENTS

| 2,891,855 | 6/1959 | Tysin et al. | 71/93 |
| 3,036,130 | 5/1962 | Jackson et al. | 568/625 |
| 3,740,421 | 6/1973 | Schmolka | 424/65 |
| 4,464,524 | 8/1984 | Karickhoff | 526/313 |
| 4,745,230 | 5/1988 | Otten et al. | 568/625 |

FOREIGN PATENT DOCUMENTS

| 0538843 | 3/1957 | Canada | 568/625 |
| 7227938 | 7/1972 | Japan | 71/DIG. 1 |

Primary Examiner—Richard L. Raymond
Assistant Examiner—Jessica H. Nguyen

[57] ABSTRACT

New liquid thickeners for aqueous liquids, particularly those employed in pesticides and latex paints, comprise polyoxyalkylene polyethers terminated with oxypropylene groups. These copolymers are prepared by reacting ethylene oxide with an active hydrogen-containing initiator having about 1 to 18 carbon atoms and at least one active hydrogen atom followed by reaction with propylene oxide.

10 Claims, No Drawings

THICKENING AQUEOUS SYSTEMS

This is a continuation-in-part of application Ser. No. 840,432 filed March 17, 1986.

BACKGROUND OF THE INVENTION

This invention relates to thickeners for aqueous systems based upon polyethers. More specifically this invention relates to thickeners for aqueous systems, particularly aqueous pesticide systems and latex paint systems.

Polymeric water soluble thickening agents are widely used for many purposes. Commercially available polymeric thickeners differ widely in chemical composition. The diversity of available thickening agents is an indication that not all are equally useful. It is not unusual to find some thickening agents which perform well in a certain environment and not at all in another environment. In fact, in some uses, no one thickening agent is completely satisfactory and there is a continual need and a continuing search for new thickening agents to satisfy many unmet needs. For instance, various cellulose derivatives or other water soluble polymers such as sodium polyacrylates, polyacrylamides and polyethylene glycol fatty acid diesters are representative thickening agents. The polyethylene glycol fatty acid diesters are widely used for textile printing emulsions, cosmetic emulsions, and aqueous pigment suspensions. Polyoxyalkylene compounds including high molecular weight materials are well known for use as surface active agents as disclosed in U.S. Patent 2,674,619.

Current technology for the preparation of aqueous dispersions of pesticides requires the inclusion of a thickener, the most successful of which at present appear to be the use of a vegetable gum or inorganic thickener to increase the viscosity (or viscous yield strength) of the formulation.

The polyoxyalkylene compounds of the type disclosed in U.S. Pat. No. 2,674,619 are useful as thickeners only with those having the highest molecular weights reasonably obtainable under commercial conditions. Because high molecular weight polyethers require a disproportionately longer processing time to produce, it would be desirable to prepare high efficiency thickeners utilizing low molecular weight polymers.

In U.S. Pat. No. 3,538,033 there are disclosed polyoxyalkylene derivatives of diepoxide having thickener properties. The thickener compositions disclosed are useful for thickening aqueous systems and are prepared by reacting a diepoxide compound having at least 12 carbon atoms with an alkylene oxide adduct containing from 100 to 250 moles of ethylene oxide units.

Polyoxyalkylene type thickeners are also disclosed in U.S. Pat. No. 4,354,956 and U.S. Pat. No. 4,288,639.

Pesticide compositions incorporating nonionic surfactants including oxyalkylene polymers and copolymers, particularly oxyethylene/oxypropylene copolymers, are disclosed in U.S. Pat. Nos. 4,351,753; 4,434,078; and 4,434,077.

Also the preparation of latex paints requires the use of a thickener.

SUMMARY OF THE INVENTION

New liquid thickeners for aqueous liquids, particularly those employed in pesticides and latex paints, comprise polyoxyalkylene polyethers terminated with oxypropylene groups. These copolymers are prepared by reacting ethylene oxide with an active hydrogen-containing initiator having about 1 to 18 carbon atoms and at least one active hydrogen atom followed by reaction with propylene oxide.

The new thickeners replace the vegetable gums of the prior art which are difficult to use, and also eliminate handling of an inorganic solid. Such thickeners cost less than vegetable gums and can be partially substituted for nonionic dispersants conventionally employed in pesticide formulations and latex paint formulations. These thickeners have a further advantage in that they supplement other dispersants by improving pesticide wetting and decreasing the amount of suspended material by eliminating the solid inorganic thickener. Since there is a wide range of such polymers this permits tailoring of the formulation to the preferred pesticide active ingredient and other components or the preferred latex and other components of the latex paint.

DETAILED DESCRIPTION OF THE INVENTION

This invention is directed to polyoxyalkylene polyether polyols which are terminated with oxypropylene groups. Generally the terminal atom on the chains of such compounds is a hydrogen atom which is preceded by the chain of polyoxypropylene groups. Also, such compounds may be capped by substituting a 1 to 4 carbon atom alkyl group for the hydrogen atom. However, for simplicity sake, the expression "terminated with oxypropylene groups," as used throughout the instant specification and claims, includes compounds having terminal hydrogen atoms and such terminal alkyl groups.

A preferred type of oxypropylene group terminated polyoxyalkylene polyether is a cogeneric mixture of conjugated polyoxyalkylene compounds containing in their structure, oxypropylene groups, oxyethylene groups, and the residue of an active hydrogen containing compound. These compounds are prepared using an active hydrogen terminated initiator which is prepared in much the same way as the polymers of U.S. Pat. No. 3,036,118 by first oxyethylating the initiator compound and subsequently oxypropylating the resulting compound to produce the nonionic surface active agent as more completely described in U.S. Pat. No. 3,036,118 incorporated herein by reference. The term "cogeneric mixture" used herein is a term that has been coined to designate a series of closely related homologues that are obtained by condensing a plurality of alkylene oxide units with a reactive hydrogen compound (see U.S. Pat. No. 2,549,438, particularly the sections beginning at column 12, line 40). This expression is well known to those skilled in the art as can be seen from U.S. Pat. Nos. 2,677,700; 2,674,619; and 2,979,528.

The active hydrogen containing compound also referred to herein as an initiator has about 1 to 18 carbon atoms, preferably about 2 to 10 carbon atoms, and at least 1, preferably about 2 to 6, active hydrogen atoms. Such initiators include ethylene glycol, propylene glycol, butylene glycol, hexyl alcohol, octyl alcohol, decyl alcohol, stearyl alcohol, ethylenediamine, triethylenediamine, hexylmethylenediamine, trimethylol propane, pentaerythritol, and erythritol. These compounds may be heteric or block, as long as they are terminated with oxypropylene groups, and are characterized in that the oxyalkylene groups are attached to the initiator compound at the site of the reactive hydrogen atoms.

In one preferred embodiment of this invention, the oxyalkylene compounds are those of the type disclosed in U.S. Pat. No. 3,036,118 prepared by first oxyethylating an initiator compound and subsequently oxypropylating the resulting compound as more completely described in said patent, incorporated herein by reference. In such compounds the polyoxyethylene groups are present in polyoxyethylene chains that are attached to the initiator nucleus at the site of the reactive hydrogen atoms thereby constituting a polyoxyethylene polymer. The oxypropylene groups are attached to the polyoxyethylene polymer in oxypropylene chains. The oxypropylene chains optionally but advantageously contain small amounts of ethylene oxide and the oxyethylene chains optionally but advantageously contain small amounts of other alkylene oxides such as propylene oxide and butylene oxide. Such compounds are believed to correspond to the formula $$Y[(C_2H_4O)_m (C_3H_6O)_n]_xH \qquad I$$

wherein Y is the residue of an organic compound having from about 1 to 18, preferably about 2 to 10 carbon atoms and containing x reactive hydrogen atoms in which x has a value of at least one, preferably about 2 to 6, n has a value such that the oxypropylene content of the molecules is from about 90 to 20 weight percent and m has a value such that the oxyethylene content of the molecule is from about 10 to 80, preferably about 20 to 40 weight percent.

It is further to be noted that when molecular weight is stated in this specification and claims, unless otherwise noted, there is meant the average theoretical molecular weight which equals the total of the grams of the alkylene oxide employed per mole of reactive hydrogen compound. It is well recognized in the field of alkylene oxide chemistry that the polyoxyalkylene compositions one obtains by condensing an alkylene oxide with a reactive hydrogen compound are actually mixtures of compounds rather than a single molecular compound. The mixture contains closely related homologues wherein the statistical average number of oxyalkylene groups equals the number of moles of the alkylene oxide employed and the individual members in the mixtures contain varying numbers of oxyalkylene groups. Accordingly, as already noted, the oxypropylene chains optionally but advantageously contain small amounts of ethylene oxide and the oxyethylene chains optionally but advantageously contain small amounts of alkylene oxides such as propylene oxide and butylene oxide Thus the compositions employed in this invention are mixtures of compounds which are defined by molecular weight of the polyoxypropylene chains and weight percent of oxyethylene groups Preferred compounds of the type of formula I are those where Y is a residue of ethylene glycol whereby the formula then becomes $$HO(C_3H_6O)_n(C_2H_4O)_m(C_3H_6O)_nH \qquad II$$

wherein n has a value such that the oxypropylene content of the polyol is from about 90 to 20 weight percent, and m has a value such that the oxyethylene content of the molecule is from about 10 to 80, preferably about 20 to 40 weight percent.

Within the broad disclosure of U.S. Pat. No. 3,036,118 nitrogen-containing polyoxyalkylene compositions are included which are similar to those described in U.S. Pat. No. 2,979,528, incorporated herein by reference, with the exception that the positions of the oxyethylene and oxypropylene chains are reversed. These compositions are prepared in much the same way as those disclosed in accordance with the procedure disclosed in U.S. Pat. No. 3,036,118. However, instead of ethylene glycol as an initiator, a reactive hydrogen compound containing nitrogen is utilized. Initiators for these compounds include ammonia, primary amines, alkylene polyamines, alkanol amines, hetrocyclic nitrogen compounds and compounds such as alkylene polyamines. Aliphatic primary diamines, having not over 6 carbon atoms are the preferred nitrogen-containing reactive hydrogen compounds and include ethylene diamine, diethylene triamine, triethylene tetramine, tetraethylene pentamine, hexamethylene diamine, phenylene diamine and the like.

Useful nitrogen-containing nonionic polyoxyalkylene compositions are mixtures of conjugated polyoxyethylene polyoxypropylene compounds based on a nitrogen-containing reactive hydrogen compound wherein chains of oxyethylene groups having a defined molecular weight are attached to the nucleus of the reactive hydrogen compound at the sites of the hydrogen atoms and wherein the chains of oxypropylene groups are attached to the opposite end of the oxyethylene chains. The compositions are prepared by condensing ethylene oxide with a nitrogen-containing reactive hydrogen compound, preferably ethylenediamine and subsequently condensing propylene oxide with the ethylene oxide-reactive hydrogen compound. The oxypropylene content of the molecules is from about 90 to 20 weight percent and the oxyethylene content of the molecule is from about 10 to 80 weight percent. Where ethylenediamine is the reactive hydrogen compound, these compounds are believed to have the following formula:

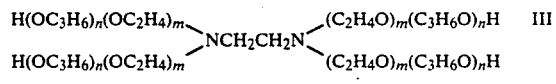

wherein n has a value such that the oxypropylene content of the molecules is from about 90 to 20 weight percent and m has a value such that the oxyethylene content of the molecule is from about 10 to 80, preferably 20 to 40 weight percent.

The process for thickening aqueous suspensions of hydrophobic particles, as well as the latex and pesticide compositions of the present invention, utilize the associative thickeners which are the preceeding polyoxyalkylene compositions. The useful polyoxyalkylene compositions have an average molecular weight range of from about 1900 to 12,000 and a hydrophilic content of from about 10 to 80 weight percent. Depending upon whether the polyoxyalkylene composition is a diol, triol or tetrol, the following provisos apply:

(a) If the polyol is a diol;
  (1) when the hydrophilic content is about 10 weight percent, the average molecular weight of the polyol is about 1,900 to 3,300;
  (2) when the hydrophilic content is about 20 to 40 weight percent, the average molecular weight of the polyol is from about 1,900 to 6,000;
  (3) when the hydrophilic content is about 50 weight percent, the average molecular weight of the polyol is from about 1,900 to 4,500;
  (4) when the hydrophilic content is about 60 weight percent, the average molecular weight of the polyol is from about 1,900 to 4,000;

(5) when the hydrophilic content is about 70 weight percent, the average molecular weight of the polyol is from about 1,900 to 3,400, and;

(6) when the hydrophilic content is about 80 weight percent, the average molecular weight of the polyol is from about 1,900 to 2,700;

(b) If the polyol is a triol;

(1) when the hydrophilic content is about 10 weight percent, the average molecular weight of the polyol is from about 2,850 to 4,950;

(2) when the hydrophilic content is about 20 to 40 weight percent, the average molecular weight of the polyol is from about 2,850 to 9,000;

(3) when the hydrophilic content is about 50 weight percent, the average molecular weight of the polyol is from about 2,850 to 6,750;

(4) when the hydrophilic content is about 60 weight percent, the average molecular weight of the polyol is from about 2,850 to 6,000;

(5) when the hydrophilic content is about 70 weight percent, the average molecular weight of the polyol is from about 2,850 to 5,100, and;

(6) when the hydrophilic content is about 80 weight percent, the average molecular weight of the polyol is from about 2,050 to 4,050, and;

(c) If the polyol is a tetrol;

(1) when the hydrophilic content is about 10 weight percent, the average molecular weight of the polyol is from about 3,800 to 6,600;

(2) when the hydrophilic content is from about 20 to 40 weight percent, the average molecular weight of the polyol is from about 3,800 to 12,000;

(3) when the hydrophilic content is about 50 weight percent, the average molecular weight of the polyol is from about 3,800 to 9,000;

(4) when the hydrophilic content is from about 60 weight percent, the average molecular weight of the polyol is from about 3,800 to 8,000;

(5) when the hydrophilic content is from about 70 weight percent, the average molecular weight of the polyol is from about 3,800 to 6,800, and;

(6) when the hydrophilic content is about 80 weight percent, the average molecular weight of the polyol is from about 3,800 to 5,400.

Pesticide compositions employing the thickener of this invention generally also include conventional additives employed in such compositions. More specifically, a preferred pesticide composition comprises about 20 to 70 percent of at least one active pesticide component, about 1 to 10 percent oxypropylene group terminated polyether polyol thickener, balance water and conventional pesticide additives in normal amounts. Preferred amounts of the latter are about 40 to 65 percent of the pesticide composition. Conventional pesticide additives include conventional nonionic surfactants, wetting agents, anionic dispersants, antifoam agents and freezing point dispersants.

As used herein, the term pesticide is intended to refer to toxicants and to biological compositions containing such chemicals which are effective in killing, preventing, or controlling the growth of undesirable pests, e.g. plants, insects, mites, microorganisms, algae, fungi, bacteria, and the like, said chemicals and compositions being commonly known as insecticides, mitocides, bactericides, algicides, fungicides, nematocides, herbicides, etc. Examples of specific known toxicants which may be employed in the composition of the invention are disclosed in U.S Pat. No. 3,948,636, which disclosure is incorporated herein by reference.

More particularly the pesticides are selected from any of the known pesticides, particularly herbicides and insecticides. Particularly useful are herbicides such as 2-chloro-2'-6'-diethyl-N(methoxymethyl)-acetanilide; a,a,a-trifloro-2,6-dinitro-N,N-dipropyl-p-toluidine and N-(1-ethylpropyl)-3,4-dimethyl-2,6-dinitrobenzenamine. Other useful biocides are listed in U.S. Pat. No. 3,317,305 incorporated herein by reference. Preferred pesticides include the following, identified first by the trademark, followed by the chemical name.

| Atrazine | 2-chloro-4-ethylamino-6-isopropylamino-1,3,5-trazine |
|---|---|
| Linuron | 3-(3,4-dichlorophenyl)-1-methoxy-1-methylurea |
| Diuron | 3-(3,4-dichlorophenyl)-1,1-dimethylurea |
| Methoxychlor | 2,2-bis(p-methoxyphenyl)-1,1,1-trichloroethane |
| Carbaryl | 1-naphthyl-N-methylcarbamate |

The conventional surfactant, generally one which is terminated with oxyethylene groups, falls in two classes: 1. Surfactants that form micelles (alcohol ethoxylates, nonylphenol ethoxylates) can increase the effectiveness of associative thickeners. 2. Surfactants that do not form micelles which weaken the associative thickener strength of the thickeners employed according to the instant invention. However they serve a purpose in that by controlling the ratio and by proper selection of such surfactants, the degree of thickening may be controlled by the combination of such surfactants with the thickener of the invention.

The conventional surface active agents of both types which are advantageously employed in accordance with the instant invention can be the polyoxyalkylene adducts of hydrophobic bases wherein the oxygen/carbon atom ratio in the oxyalkylene portion of the molecule is greater than 0.40. Those compositions which are condensed with hydrophobic bases to provide a polyoxyalkylene portion having an oxygen/carbon atom ratio greater than 0.40 include ethylene oxide, butadiene dioxide and glycidol, mixtures of these alkylene oxides with each other and with minor amounts of propylene oxide, butylene oxide, alkylene oxide, styrene oxide, and other higher molecular weight alkylene oxides. Ethylene oxide, for example, is condensed with the hydrophobic base in an amount sufficient to impart water dispersibility or solubility and surface active properties to the molecule being prepared. The exact amount of ethylene oxide condensed with the hydrophobic base will depend upon the chemical characteristics of the base employed and is readily apparent to those of ordinary skill in the art relating to the synthesis of oxyalkylene surfactant condensates.

Typical hydrophobic bases which can be condensed with ethylene oxide in order to prepare nonionic surface active agents include mono- and polyalkyl phenols, polyoxypropylene condensed with a base having from about 1 to 6 carbon atoms and at least one reactive hydrogen atom, fatty acids, fatty amines, fatty amides and fatty alcohols. The hydrocarbon ethers such as the benzyl or lower alkyl ether of the polyoxyethylene surfactant condensates are also advantageously employed in the compositions of the invention.

Among the suitable nonionic surfactants are the polyoxyethylene condensates of alkyl phenols having from about 6 to 20 carbon atoms in the alkyl portion and from about 5 to 30 ethenoxy groups in the polyoxyethylene radical. The alkyl substituent on the aromatic nucleus may be octyl, diamyl, n-dodecyl, polymerized propylene such as propylene tetramer and trimer, isoctyl, nonyl, etc. The benzyl ethers of the polyoxyethylene condensates of monoalkyl phenols impart good properties to the compositions of the invention. A typical product corresponds to the formula:

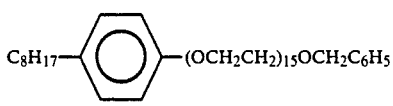

Higher polyalkyl oxyethylated phenols corresponding to the formula:

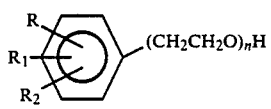

wherein R is hydrogen or an alkyl radical having from about 1 to 12 carbon atoms, $R_1$ and $R_2$ are alkyl radicals having from about 6 to 16 carbon atoms and n has a value from about 10 to 40, are also suitable as nonionic surfactants. A typical oxyethylated polyalkyl phenol is dinonyl phenol condensed with 14 moles of ethylene oxide.

Other suitable nonionic surface-active agents are co-generic mixtures of conjugated polyoxyalkylene compounds containing in their structure at least one hydrophobic oxyalkylene chain in which the oxygen/carbon atom ratio is less than 0.40.

Polymers of oxyalkylene groups obtained from propylene oxide, butylene oxide, amylene oxide, styrene oxide, mixtures of such oxyalkylene groups with each other and with minor amounts of polyoxyalkylene groups obtained from ethylene oxide, butadiene dioxide, and glycidol are illustrative of hydrophobic alkylene chains having an oxygen/carbon atom ratio not exceeding 0.40. Polymers having oxyalkylene groups obtained from ethylene oxide, butadiene dioxide, glycidol, mixtures of such oxyalkylene groups with each other and with minor amounts of oxyalkylene groups obtained from propylene oxide, butylene oxide, amylene oxide and styrene oxide are illustrative of hydrophilic oxyalkylene chains having an oxygen/carbon atom ratio greater than 0.40.

Among the conjugated polyoxyalkylene compounds which can be used in the compositions of the invention are those which correspond to the formula:

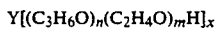

wherein Y is the residue of an organic compound having about 1 to 18 carbon atoms and containing x reactive hydrogen atoms in which x has a value of at least 1, preferably 2 to 6, n has a value such that the molecular weight of the polyoxypropylene hydrophobic base is at least about 250, preferably about 450 to 10,000, and m has a value such that the oxyethylene content of the molecule is from about 10 to 90 weight percent. These compositions are more particularly described in U.S. Pat. No. 2,674,619, incorporated herein by reference.

Further suitable nonionic surface active agents are the polyoxyethylene esters of higher fatty acids having from about 8 to 22 carbon atoms in the acyl group and from about 8 to 30 ethenoxy units in the oxyethylene portion. Typical products are the polyoxyethylene adducts of rosin acids, lauric, stearic and oleic acids and the like. Additional nonionic surface active agents are the polyoxyethylene condensates of higher fatty acid amines and amides having from about 8 to 22 carbon atoms in the fatty alkyl or acyl group and about 10 to 30 ethenoxy units in the oxyethylene portion. Illustrative products are coconut oil, fatty amines and acid amides condensed with about 10 to 30 moles of ethylene oxide.

Other suitable polyoxyalkylene nonionic surface active agents are the alkylene oxide adducts of higher aliphatic alcohols and thioalcohols having from about 8 to 22 carbon atoms in the aliphatic portion and about 3 to 50 oxyalkylene units in the oxyalkylene portion. Typical products are synthetic fatty alcohols, such as n-decyl, n-undecyl, n-dodecyl, n-tridecyl, n-tetradecyl, n-hexadecyl, n-octadecyl and mixtures thereof condensed with 3 to 50 moles of ethylene oxide; a mixture of normal fatty alcohols condensed with 8 to 20 moles of ethylene oxide and capped with benzyl halide or an alkyl halide; a mixture of normal fatty alcohols condensed with 10 to 30 moles of a mixture of ethylene and propylene oxides; a mixture of several fatty alcohols condensed sesquentially with 2 to 20 moles of ethylene oxide and 3 to 10 moles of propylene oxide in either order; or a mixture of normal fatty alcohols condensed with a mixture of propylene and ethylene oxides in which the oxygen/carbon atom ratio is less than 0.40, followed by a mixture of propylene and ethylene oxides in which the oxygen/carbon atom ratio is greater than 0.40, or a linear secondary alcohol condensed with 3 to 30 moles of ethylene oxide, or a linear secondary alcohol condensed with a mixture of propylene and ethylene oxides or a linear secondary alcohol condensed with a mixture of ethylene, propylene, and higher alkylene oxides.

Within the broad disclosure of U.S. Pat. No. 2,674,619, nitrogen-containing polyoxyalkylene compositions are included which are more particularly described in U.S. Pat. No. 2,979,528, incorporated herein by reference. These surfactants possess a unique feature, namely the ability to disperse lime soaps formed by fatty acid soaps in hard water and thus are particularly suitable for use in the surfactant blend of the invention. These compositions are prepared in much the same way as those disclosed above and more particularly in accordance with the procedure disclosed in U.S. Pat. No. 2,674,619 but instead of propylene glycol as initiator, a reactive hydrogen compound containing nitrogen is utilized. Generally, the nitrogen-containing reactive hydrogen compound has up to about six, inclusive, carbon atoms. When the nitrogen-containing reactive hydrogen compound is so defined, there still remains a reasonably broad group of such compounds which can be used. Ammonia, primary amines, alkylene polyamines, alkanolamines, heterocyclic nitrogen compounds are examples of the classes of nitrogen-containing reactive hydrogen compounds which can be used.

Thus, primary amines having not over six carbon atoms such as methylamine, ethylamine, propylamine, butylamine, amylamine, hexylamine and aniline are satisfactory. Alkylene polyamines, especially aliphatic primary diamines, having not over six carbon atoms are the preferred reactive hydrogen compounds.

Useful nitrogen-containing nonionic surfactants are mixtures of conjugated polyoxypropylene-polyoxyethylene compounds based on a nitrogen-containing reactive hydrogen compound wherein chains of oxypropylene groups having a defined molecular weight are attached to the nucleus of the reactive hydrogen compound at the sites of the reactive hydrogen atoms and wherein chains of oxyethylene groups are attached to the end of the oxypropylene chains. The compositions are prepared by condensing propylene oxide with a nitrogen-containing reactive hydrogen compound and subsequently condensing ethylene oxide with the propylene oxide-reactive hydrogen compound condensate.

The collective molecular weight of the oxypropylene chains attached to the nitrogen-containing reactive hydrogen compound must be at least about 2,000 and can range up to about 10,000 or higher.

The nitrogen-containing nonionic surfactants contain chains of oxyethylene groups attached to the oxypropylene chains. The amount of ethylene oxide employed is such that the oxyethylene groups constitute about 10 to 90 weight percent of the final composition.

The pesticide composition contains 0 to about 10 percent, preferably about 1 to 3 percent, of conventional surfactant.

The preferred anionic wetting agents are included in amounts of 0 to about 5 percent, and preferably about 1 to 3 percent and are salts of alkylnaphthalene sulfonate, particularly the sodium salts. The preferred anionic dispersant is included in amounts of about 0 to 5 percent, preferably 1 to 3 percent, and is a salt of a sulfonated naphthalene formaldehyde condensate or lignin sulfonate salt. Again, the preferred salts are sodium salts.

Freezing point depressants may be included in amounts of 0 to about 10 percent, preferably 3 to 5 percent. Glycols are the preferred freezing point depressants, particularly ethylene glycol, or propylene glycol.

Any conventional antifoam may be employed in amounts of 0 to about 5 percent, preferably 0.1 to 1 percent.

It is to be understood of course that various conventional adjuvants conventionally employed in pesticide compositions may also be incorporated into the composition when needed for specific uses.

Latex paint vehicles are discreet, small particles of polymer suspended in water. They are formed by emulsion polymerization, i.e. by introducing a liquid monomer into water and causing polymerization of that monomer within small droplets. Because the continuous phase, i.e., water, is not very viscous, the paint must be thickened with an additive to promote suspension of the pigment and polymer during storage, and proper rheology for application and flow without sagging. Cellulosic thickeners, e.g., hydroxyethyl cellulose or carboxymethyl cellulose, are used most commonly, and they function very well as pigment suspenders in the package. However, they allow excessive viscosity breakdown under shear, thereby causing excessive spread in latex paints for adequate coverage.

It is expected that the thickener employed in this invention would produce excellent results in such latex paints. The thickener of the instant invention is added to a latex paint composition in an amount sufficient to produce a composition comprising about 1 to 80 percent conventional latex paint composition, about 0.5 to 40 percent polyoxyalkylene ether polyol thickener, balance water. A preferred latex paint composition comprises 1 to 40 percent pigment, 0.5 to 40 percent thickener, balance water and conventional latex paint additives in normal amounts. Such compositions are well known to those skilled in the art and are described in the Kirk-Othmer *Encyclopedia of Chemical Technology*, vol. 16, Paint, pages 748–751, incorporated herein by reference.

Typical latex paint compositions are as follows:

| Flat Interior Latex Paint | |
|---|---|
| Thickener #1 | 8 |
| Vancide ® TH | 1 |
| Darvan ® No. 7 | 15 |
| Ethylene Glycol | 25 |
| Texanol | 12 |
| Defoamer | 2 |
| Titanium Dioxide | 150 |
| Nytal ® 300 | 310 |
| Water | 417 |
| Aerosol ® OT-B (5% soln.) | 20 |
| Vinyl-Acrylic Latex | 210 |
| Dripfree Acrylic Latex Paint | |
| Thickener #2 | 336 |
| Vancide ® TH | 1 |
| Ethylene Glycol | 25 |
| Darvan ® No. 7 | 10 |
| Antifoamer | 4 |
| Ammonium Hydroxide (28%) | 2 |
| Titanium Dioxide | 200 |
| Nytal ® 300 | 225 |
| Rhoplex ® AC-33 | 327 |
| Wetting Agent | 20 |
| Acrylic Latex Paint (Interior Blue) | |
| Rutile Titania | 230.00 |
| Thickener #3 | 144.70 |
| ASP ® 400 | 57.20 |
| Phthalocyanine Blue Toner | 12.61 |
| Surfynol ® TG | 1.76 |
| Tamol ® 731 (100% basis) | 1.09 |
| Potassium Carbonate | 1.78 |
| Rhoplex ® AC-33 | 440.00 |
| Water | 218.00 |

In the above formulations.
VANCIDE TH is a trademark of the R. T. Vanderbilt Company, Inc. covering a mitocide.
DARVAN No. 7 is a trademark of the R. T. Vanderbilt Company, Inc. covering a dispersant, more specifically sodium polymethacrylate.
TEXANOL is a trademark of the Eastman Chemicals Company and covers 2,2,4-trimethyl-1,3-pentanediol mono-isobuterate (paint solvent).
NYTAL 300 is a trademark of the R. T. Vanderbilt Company, Inc. covering a talc extender pigment.
Aerosol OT-B is a trademark of American Cyanamid Company covering a dispersant, more specifically dioctyl ester of sodium sulfosuccinic acid.
ASP-400 is a trademark of the Engelhard Minerals and Chemicals Company for a hydroxy kaolin filler.
SURFYNOL TG is a trademark of Air Products Company covering a surfactant.
TALMOL 731 is a trademark of the Rohm and Haas Company covering a dispersant, more specifically sodium salt of polymeric carboxylic acid.
RHOPLEX AC-33 is a trademark of the Rohm and Haas Company covering an acrylic emulsion, more specifically an alkyl acrylate copolymer.

In the above formulations, thickener No. 1 defines the polyoxypropylene adduct of a polycxyethylene hydrophobic base having a molecular weight of the hydrophobic base of about 1700 wherein the oxyethylene content is about 40 weight percent of the molecule.

Thickener No. 2 defines the polyoxypropylene adduct of a polyoxyethylene hydrophobic base having a molecular weight of the hydrophobic base of about 2,500 wherein the oxyethylene content is about 20 percent of the molecule.

Thickener No. 3 is the polyoxyethylene adduct of a polyoxypropylene ethylenediamine condensate wherein the Oxypropylene hydrophobic base has a molecular weight of about 7,200 and the oxyethylene content is about 30 weight percent of the molecule.

The invention as applied to insecticide formulations is illustrated by the following specific examples. Throughout the specification and claims all parts are by weight and temperatures are in degrees Centigrade unless otherwise specifically indicated.

ing examples is attached to a Brookfield viscometer, Model LVF. This is a well-known device to those skilled in the art and is readily available on the market. The spindle is inserted into the sample and the viscometer is allowed to run at specified speed for 10 to 20 turns and then stopped and the viscosity recorded.

TABLE I

| Example No. | 1<br>Nonionic #1 3.5<br>No Thickener | 2<br>Nonionic #1 3.5<br>Xanthine Gum 0.5<br>MgALSiO$_x$ 0.20 | 3<br>Nonionic #1 1.0<br>Nonionic #2 2.5 | 4<br>Nonionic #1 1.0<br>Nonionic #3 2.5 |
|---|---|---|---|---|
| Brookfield LVF Spindle #3 | | | | |
| 6 rpm | 860 | 3840 | 4040 | 5580 |
| 12 rpm | 540 | 2160 | 2370 | 3030 |
| 30 rpm | 328 | 1152 | 1184 | 1744 |
| 60 rpm | 208 | 726 | 772 | 1200 |

EXAMPLES 1-4

These examples illustrate the combination of a surfactant that forms micelles with a prior art thickener and thickeners of the instant invention. More specifically a base composition was prepared comprising by weight 46 percent Atrazine biocide, 5.0 percent ethylene glycol, 1.0 percent sodium alkyl naphthalene sulfonate wetting agent, 2.0 percent sodium salt of sulfonated naphthalene formaldehyde condensate dispersant, 0.1 percent Dow Corning FG-10 antifoam, balance water to make 100 percent.

A conventional nonionic surfactant and a thickener were added to this base composition in the amounts shown in Table I below. The conventional nonionic is designated as nonionic No. 1 and is a nonylphenol ethoxylate obtained from the reaction of 9 moles of ethylene oxide with one mole of nonylphenol.

Nonionic No. 2, is a thickener in accordance with the instant invention and defines a block copolymer, which is the polyoxypropylene adduct of a polyoxyethylene base, i.e. comprises polyoxypropylene groups at both ends of a polyoxyethylene base. The molecular weight of the polyoxypropylene groups is about 1700 and the percent oxyethylene groups is 20 weight percent of the molecule.

Nonionic No. 3 is a thickener employed in accordance with the instant invention and defines a block copolymer which is the polyoxypropylene adduct of a polyoxyethylene base, i.e. comprises polyoxypropylene groups at both ends of a polyoxyethylene base. The molecular weight of the polyoxypropylene groups is about 3100 and the oxyethylene content is about 10 weight percent of the molecule. The percentage of each additive component shown in Table I below is a percent of the weight of the base composition described above. Each composition was tested for Brookfield viscosity as follows:

The Brookfield viscometer rotates a spindle in the liquid and measures the torque necessary to overcome the resistance to the induced movement at a specific temperature. More specifically, the sample to be tested is placed in a 250 milliliter beaker. The sample should be obtained in the sample container used for the test to avoid any necessity for mixing the sample before testing and reducing the possibility of air bubble inclusion and then is allowed to stand until any occluded air bubbles have disappeared. The sample and container are then placed in a water bath which is maintained at a constant temperature of 25° C. % 0.1° C. in such a manner that the sample level is below the level of the bath. The preferred spindle, which is spindle No. 3 for the follow-

EXAMPLES 5-7

These examples illustrate the combination of a conventional nonionic that does not form micelles, i.e. nonionic No. 4 with a nonionic thickener of the instant invention. The compositions of Examples 5, 6, and 7 shown in Table II below were each mixed with the base composition described above, the percentages of each component in Table II being in percent based on the weight of the base composition. These compositions were subjected to Brookfield viscosity tests as described in connection with Example 1-4 and the results are set forth below in Table II. In the table, nonionic No. 4 is a conventional nonionic, i.e. an oxyethylene group terminated nonionic which defines a block copolymer which is the polyoxyethylene adduct of a polyoxypropylene hydrophobic base, i.e. comprises polyxoyethylene groups at both ends of a polyoxypropylene base. The molecular weight of the hydrophobic base is about 3,250 and the oxyethylene content is about 40 weight percent of the molecule.

Nonionic No. 5 defines a block copolymer which is the polyoxypropylene adduct of a polyoxyethylene base, i.e. comprises polyoxypropylene groups at both ends of a polyoxyethylene base. The molecular weight of the polyoxypropylene groups is about 3,100 and the oxyethylene content is about 20 weight percent of the molecule. The results of the Brookfield viscosity tests are set forth below in Table II.

TABLE II

| Example No. | 5<br>Nonionic #4 1.0<br>Nonionic #3 2.5 | 6<br>Nonionic #4 0.5<br>Nonionic #3 3.0 | 7<br>Nonionic #4 0.25<br>Nonionic #5 2.75 |
|---|---|---|---|
| Brookfield LVF Spindle #3 | | | |
| 6 rpm | 900 | Too | 2740 |
| 12 rpm | 650 | Thixotropic | 1620 |
| 30 rpm | 328 | | 956 |
| 60 rpm | 208 | | 668 |

EXAMPLES 7 through 10

The surfactants of the prior art were compared with those of the present invention in a standard Atrazine formulation given in Table III. The prior art surfactants compared were a polyoxyethylene polyoxypropylene block copolymer identified as S-17 and polyoxypropylene polyoxyethylene block copolymers identified as S-1 through S-16. Their composition is given in Tables IV and V. Among the polyoxypropylene/polyoxyethylene copolymers, those designated as S-2, S-4, S-6, S-8, S-10, S-11, S-15 and S-16 are among those of the present invention.

The formulation, as seen in Table III was prepared by combining the liquid ingredients in an Attritor Model 01 mill. The water soluble materials were dissolved and powdered Atrazine was added in the milling process. Following addition of the Atrazine, the suspensions were milled for one (1) hour. All of the suspensions were stored for three to four weeks at approximately 20° C. to allow entrapped air to escape. Any entrapped air would lead to erroneous viscosity measurements. Viscosity measurements were made with a Brookfield Model LVF Viscometer using a #3 spindle at 20° C. The resulting viscosity values at 6 rpm (low shear) and 60 rpm (high shear) are given in Tables IV and V, respectively.

Tables IV and V show the relationship of the weight percent of the polyoxyethylene hydrophile of the molecule to the average molecular weight of polyoxypropylene hydrophobe.

The data contained in Tables IV and V demonstrate that only some of the surfactants possess thickening properties. The thickening is relative to the length of the hydrophobe and the percent hydrophile of the thickener. If the hydrophobe is too long, it will tend to fold over on itself and form a vesicle, thereby losing the ability to act as an associative thickener. Similarly, if the hydrophilic portions are too long, a vesicle will result with a similar loss of thickening ability. The data indicated that there is a clear range of effective thickening which is greater than about 2500 mPas at 6 rpm and greater than about 700 mPas at 60 rpm.

Table VI depicts the viscosities of the Atrazine flowable of the present invention. Again, the viscosity was measured first at 6 rpm and then at 60 rpm with a Brookfield LVF Viscometer Spindle #3. As demonstrated in the tables, there was an associative thickening action of the polyol on the formulation. The thickeners used were the same as in Tables IV and V. Also included was a polyoxyethylene/polyoxypropylene block copolymer having an approximate molecular weight of about 12,600 and a hydrophile content of about 70 weight percent, which is identified as S-17 and which functions as a gel thickener.

As can be seen, only the polyoxypropylene/polyoxyethylene block copolymers of the present invention functioned as an associative thickener, and the polyoxyethylene/polyoxypropylene block copolymer did not thicken the formulation, but rather thinned the formulation. Thus, it is evident that only associative thickeners will thicken the Atrazine formulation and gel thickeners of the prior art actually thin the formulation.

TABLE III

| Basic Formulation | | |
|---|---|---|
| Water | 42.4 | Continuous Phase |
| Ethylene Glycol | 5.0 | Antifreeze, Continuous Phase |
| Silicone Antifoam | 0.1 | Antiform |
| Nonylphenol 9EO Surfactant | 1.0 | Nonionic Wetting Agent |
| Basowet BX | 1.0 | Anionic Wetting Agent |
| Vultamol NNO | 2.0 | Anionic Dispersant |
| Atrazine | 46.0 | Material Being Dispersed |
| VARIABLE | 2.5 | |
| | 100.0 | |

Variables Used in Study
(a) Polyoxypropylene/polyoxyethylene block copolymers identified as S-1 through S-16.
(b) Polyoxyethylene/polyoxypropylene block copolymer identified as S-17.
(c) Distilled Water

TABLE IV

Thickening of Atrazine Suspensions:
Measurement of Viscosities in (mPas) at 6 RPM (Low Shear)

| Sample | Average Molecular Wt. | Approx. Combined Polyoxypropylene Hydrophobe wt. | Approx. Combined Polyoxyethylene Hydrophile wt. % | Thickened Atrazine Suspension | Viscosity in mPas |
|---|---|---|---|---|---|
| S-1 | 1950 | 50% | 50% | no | 1300 |
| S-2 | 4550 | 20% | 80% | yes | 4800 |
| S-3 | 1800 | 80% | 30% | no | 1300 |
| S-4 | 1900 | 90% | 10% | yes | 8500* |
| S-5 | 2150 | 80% | 20% | no | 1900 |
| S-6 | 2650 | 60% | 40% | yes | 2800 |
| S-7 | 7000 | 20% | 80% | No | 2200 |
| S-8 | 3350 | 60% | 40% | yes | 4100 |
| S-9 | 2700 | 90% | 10% | no | 1360 |
| S-10 | 3100 | 80% | 20% | yes | 4600 |
| S-11 | 3600 | 60% | 40% | yes | 4800 |
| S-12 | 4250 | 50% | 50% | Not observed | Not measured |
| S-13 | 8550 | 20% | 80% | no | 1000 |
| S-14 | 3250 | 90% | 10% | no | 2100 |
| S-15 | 3300 | 80% | 20% | yes | 3800 |
| S-16 | 4150 | 60% | 40% | yes | 5000 |

*NOTE:
Viscosity data for S-4 is meaningless because a Brookfield Spindle #4 was used instead of a Brookfield Spindle #3.

TABLE V

Thickening of Atrazine Suspensions:
Measurement of Viscosities in (mPas) at 6 RPM (High Shear)

| Sample | Average Molecular Wt. | Approx. Combined Polyoxypropylene Hydrophobe wt. | Approx. Combined Polyoxyethylene Hydrophile wt. % | Thickened Atrazine Suspension | Viscosity in mPas |
|---|---|---|---|---|---|
| S-1 | 1950 | 50% | 50% | no | 230 |
| S-2 | 4550 | 20% | 80% | yes | 760 |

TABLE V-continued

Thickening of Atrazine Suspensions:
Measurement of Viscosities in (mPas) at 6 RPM (High Shear)

| Sample | Average Molecular Wt. | Approx. Combined Polyoxypropylene Hydrophobe wt. | Approx. Combined Polyoxyethylene Hydrophile wt. % | Thickened Atrazine Suspension | Viscosity in mPas |
|---|---|---|---|---|---|
| S-3 | 1800 | 70% | 30% | no | 240 |
| S-4 | 1900 | 90% | 10% | yes | 110* |
| S-5 | 2150 | 80% | 20% | no | 470 |
| S-6 | 2650 | 60% | 40% | yes | 716 |
| S-7 | 7000 | 20% | 80% | no | 506 |
| S-8 | 3350 | 60% | 40% | yes | 1060 |
| S-9 | 2700 | 90% | 10% | no | 246 |
| S-10 | 3100 | 80% | 20% | yes | 1190 |
| S-11 | 3600 | 60% | 40% | yes | 1660 |
| S-12 | 4250 | 50% | 50% | Not observed | Not measured |
| S-13 | 8550 | 20% | 80% | no | 280 |
| S-14 | 3250 | 90% | 10% | no | 570 |
| S-15 | 3300 | 80% | 20% | yes | 1080* |
| S-16 | 4150 | 60% | 40% | yes | 1490 |

*NOTE:
Viscosity data for S-4 is meaningless because a Brookfield Spindle #4 was used instead of a Brookfield Spindle #3.

TABLE VI

Variable vs Brookfield Viscosity (mPas) (Rm Temp: Spindle 3)

| VARIABLE SAMPLE | Viscosity (mPas) 6 rpm | 60 rpm |
|---|---|---|
| **S-1 | 1300 | 230 |
| *S-2 | 4200 | 760 |
| **S-3 | 1300 | 200 |
| **S-4 | — | — out of range |
| **S-5 | 1900 | 470 |
| *S-6 | 2800 | 716 |
| **S-7 | 2200 | 506 |
| *S-8 | 4100 | 1060 |
| **S-9 | 1360 | 296 |
| *S-10 | 3800 | 1080 |
| *S-11 | 4800 | 1060 |
| **S-13 | 1000 | 280 |
| **S-14 | 2100 | 570 |
| *S-15 | 3800 | 1080 |
| *S-16 | 5000 | 1490 |
| distilled H₂O | 335 | 93 |
| ***S-17 | 200 | 48 |

*Associative thickeners of the present invention.
**Representative polyoxypropylene/polyoxyethylene block copolymer surface active materials.
***Representative polyoxyethylene/polyoxypropylene block copolymer thickener.
NOTE: The data regarding S-4 is meaningless because a Brookfield Spindle #4 was used to measure viscosity instead of a Brookfield Spindle #3.

While there has been shown and described herein certain embodiments of the present invention, it is intended that there be covered as well any change or modification therein which may be made without departing from the spirit and scope thereof.

What is claimed is:

1. A thickened aqueous pesticide composition comprising an active pesticide component and a thickening effective amount of an oxypropylene group terminated polyoxyalkylene polyether polyol thickener which is a cogeneric mixture of conjugated polyoxyalkylene compounds containing in their structure oxyethylene groups, oxypropylene groups, and the nucleus of an active hydrogen-containing organic compound having about 1 to 18 aliphatic carbon atoms and about 2 hydrogen atoms wherein the oxyethylene groups are present in polyoxyethylene chains that are attached to the nucleus at the site of the reactive hydrogen atoms and the oxypropylene groups are attached to oxyethylene groups at the end opposite the end of said oxyethylene groups which are attached to the nucleus, said polyoxyalkylene polyol having an average molecular weight range from about 1,900 to 12,000, a hydrophilic content of from about 10 to 80 weight percent and a hydrophobic content of from 90 to 20 weight percent, with the provisos that:

(a) If the polyol is a diol;
 (1) when the hydrophilic content is about 10 weight percent, the average molecular weight of the polyol is about 1,900 to 3,300;
 (2) when the hydrophilic content is about 20 to 40 weight percent, the average molecular weight of the polyol is from about 1,900 to 6,000;
 (3) when the hydrophilic content is about 50 weight percent, the average molecular weight of the polyol is from about 1,900 to 4,500;
 (4) when the hydrophilic content is about 60 weight percent, the average molecular weight of the polyol is from about 1,900 to 4,000;
 (5) when the hydrophilic content is about 70 weight percent, the average molecular weight of the polyol is from about 1,900 to 3,400; and,
 (6) when the hydrophilic content is about 80 weight percent, the average molecular weight of the polyol is from about 1,900 to 2,700;

(b) If the polyol is a triol;
 (1) when the hydrophilic content is about 10 weight percent, the average molecular weight of the polyol is from about 2,850 to 4,950;
 (2) when the hydrophilic content is about 20 to 40 weight percent, the average molecular weight of the polyol is from about 2,850 to 9,000;
 (3) when the hydrophilic content is about 50 weight percent, the average molecular weight of the polyol is from about 2,850 to 6,750;
 (4) when the hydrophilic content is about 60 weight percent, the average molecular weight of the polyol is from about 2,850 to 6,000;
 (5) when the hydrophilic content is about 70 weight percent, the average molecular weight of the polyol is from about 2,850 to 5,100, and;
 (6) when the hydrophilic content is about 80 weight percent, the average molecular weight of the polyol is from about 2,050 to 4,050, and;

(c) If the polyol is a tetrol;
 (1) when the hydrophilic content is about 10 weight percent, the average molecular weight of the polyol is from about 3,800 to 6,600;

(2) when the hydrophilic content is from about 20 to 40 weight percent, the average molecular weight of the polyol is from about 3,800 to 12,000;

(3) when the hydrophilic content is about 50 weight percent, the average molecular weight of the polyol is from about 3,800 to 9,000;

(4) when the hydrophilic content is from about 60 weight percent, the average molecular weight of the polyol is from about 3,800 to 8,000;

(5) when the hydrophilic content is from about 70 weight percent, the average molecular weight of the polyol is from about 3,800 to 6,800, and;

(6) when the hydrophilic content is about 80 weight percent, the average molecular weight of the polyol is from about 3,800 to 5,400.

2. The composition of claim 1 comprising about 20 to 70 percent active pesticide component, 1 to 10 percent polyoxyalkylene polyether polyol thickener, balance water and conventional pesticide additives in normal amounts.

3. The composition of claim 1 wherein said composition also includes an oxyethylene group terminated polyoxyalkylene polyether polyol.

4. The composition of claim 3 wherein said pesticide composition includes naphthalene sulfonates.

5. The composition of claim 4 including about 1.0 to 10 percent oxyethylene group terminated polyoxyalkylene polyether polyol and about 1.0 to 10 percent naphthalene sulfonate compound.

6. A thickened aqueous pesticide composition comprising an active pesticide component and a thickening effective amount of an oxypropylene group terminated polyoxyalkylene polyether polyol thickener which is a cogeneric mixture of conjugated polyoxyalkylene compounds containing in their structure oxyethylene groups, oxypropylene groups, and ethylenediamine wherein the oxyethylene groups are present in polyoxyethylene chains that are attached to the nucleus at the site of the reactive hydrogen atoms of the ethylenediamine and the oxypropylene groups are attached to oxyethylene groups at the end opposite the end of said oxyethylene groups which are attached to the nucleus, said polyoxyalkylene polyol having a molecular weight of from about 3,800 to 12,000 and a percent oxyethylene groups is from about 10 to 80 weight percent and the hydrophobic content is from about 90 to 20 weight percent, with the provisos that:

(1) when the hydrophilic content is about 10 weight percent, the average molecular weight of the polyol is about 3,800 to 12,000;

(2) when the hydrophilic content is from about 20 to 40 weight percent, the average molecular weight of the polyol is from about 3,800 to 12,000;

(3) when the hydrophilic content is about 50 weight percent, the average molecular weight of the polyol is from about 3,800 to 9,000;

(4) when the hydrophilic content is from about 60 weight percent, the average molecular weight of the polyol is from about 3,800 to 8,000;

(5) when the hydrophilic content is from about 70 weight percent, the average molecular weight of the polyol is from about 3,800 to 6,800, and;

(6) when the hydrophilic content is about 80 weight percent, the average molecular weight of the polyol is from about 3,800 to 5,400.

7. The composition of claim 1 comprising about 20 to 70 percent active pesticide component, about 1.0 to 10 percent of said polyoxyalkylene polyether polyol thickener, balance water and conventional pesticide additives in normal amounts.

8. The composition of claim 7 wherein said composition also includes an oxyethylene group terminated polyoxyalkylene polyether polyol.

9. The process of claim 8 wherein said pesticide composition includes naphthalene sulfonate compounds.

10. The composition of claim 9 including about 1.0 to 10 percent oxyethylene group terminated polyoxyalkylene polyether polyol and about 1.0 to 10 percent naphthalene sulfonate compound.

* * * * *